United States Patent [19]

Schneider et al.

[11] Patent Number: 5,276,024
[45] Date of Patent: Jan. 4, 1994

[54] 3-SUBSTITUTED CEPHALOSPORINS, AND THEIR USE AS MEDICAMENTS

[75] Inventors: Stephan Schneider; Rainer Endermann; Karl G. Metzger; Klaus-Dieter Bremm, all of Wuppertal, Fed. Rep. of Germany

[73] Assignee: Bayer Aktiengesellschaft, Leverkusen, Fed. Rep. of Germany

[21] Appl. No.: 796,110

[22] Filed: Nov. 21, 1991

[30] Foreign Application Priority Data

Nov. 28, 1990 [DE] Fed. Rep. of Germany ....... 4037841

[51] Int. Cl.⁵ .................. C07D 501/22; A61K 31/545
[52] U.S. Cl. .................................... 514/202; 540/222; 540/226; 540/227; 514/206
[58] Field of Search .................. 540/227, 225, 222; 514/202, 206

[56] References Cited

U.S. PATENT DOCUMENTS

| 3,947,413 | 3/1976 | Christensen et al. | 260/243 |
| 4,060,687 | 11/1977 | Christensen et al. | 544/27 |
| 4,258,040 | 3/1981 | Christensen et al. | 424/246 |
| 4,496,560 | 1/1985 | Fayl et al. | 540/226 |
| 4,870,168 | 9/1989 | Baker et al. | 540/222 |
| 5,043,439 | 8/1991 | Kant et al. | 540/215 |
| 5,081,116 | 1/1992 | Nagane et al. | 540/226 |

FOREIGN PATENT DOCUMENTS

| 0223184 | 5/1987 | European Pat. Off. |
| 0343277 | 11/1989 | European Pat. Off. |
| 0395219 | 10/1990 | European Pat. Off. |
| 0192210 | 10/1992 | European Pat. Off. |
| 2206085 | 6/1974 | France |

OTHER PUBLICATIONS

J. Org. Chem. 1989, 54, 4962-4966.
Tetrahedron Letters, vol. 29, No. 47, pp. 6043-6046 (1988).
Tetrahedron vol. 34, pp. 2233-2243, 1978.

*Primary Examiner*—Nicholas S. Rizzo
*Attorney, Agent, or Firm*—Sprung Horn Kramer & Woods

[57] ABSTRACT

The invention relates to new 3-substituted cephalosporins, to a process for their preparation and to their use as medicaments, in particular as medicaments having antibacterial activity.

The invention relates to compounds of the general formula (I)

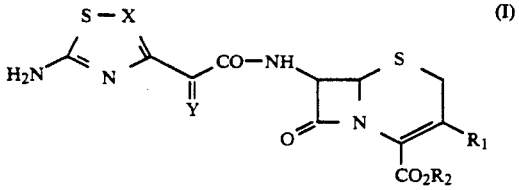

in which
X, Y, $R^1$ and $R^2$ have the meaning indicated in the description.

6 Claims, No Drawings

3-SUBSTITUTED CEPHALOSPORINS, AND THEIR USE AS MEDICAMENTS

The invention relates to new 3-substituted cephalosporins, to a process for their preparation and to their use as medicaments, in particular as medicaments having antibacterial activity.

7-Substituted cyclopropyloximino-acetamido-cephemcarboxylic acids having antibacterial activity are disclosed in EP 192,210 A2.

Moreover, 7-thiazolyl-8-butenoylamino-cephalosporin derivatives are described in EP A2 223,184.

The invention relates to compounds of the general formula (I)

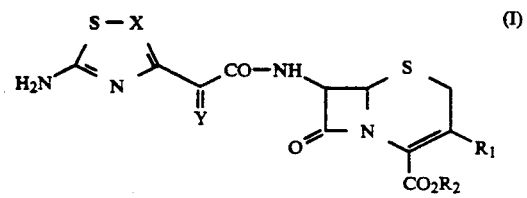

in which
X represents a nitrogen atom or the —CH group,
Y represents a group of the formula N—$OR^3$ or $CHR^4$, in which
$R^3$ denotes hydrogen, straight-chain or branched alkenyl, alkinyl or alkyl in each case having up to 8 carbon atoms, where the latter can optionally be substituted by halogen or by protected or unprotected carboxyl or amino,
$R^4$ denotes hydrogen, aryl having 6 to 10 carbon atoms, protected or unprotected carboxyl, halogen or straight-chain or branched alkoxycarbonyl, alkoxy, alkenyl or alkyl in each case having up to 8 carbon atoms, where the latter can optionally be substituted by halogen, hydroxyl, nitro, cyano or carboxyl or by straight-chain or branched alkoxy or alkoxycarbonyl in each case having up to 6 carbon atoms,
$R^1$ represents a radical of the formula

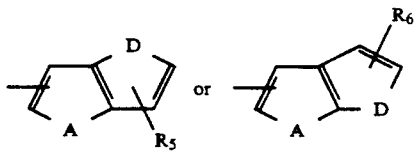

in which
A and D are identical or different and denote the group —CH=CH or an oxygen or sulphur atom, and
$R^5$ and $R^6$ are identical or different and denote halogen, trifluoromethyl, trifluoromethoxy, hydroxyl or a group of the formula —$NR^7R^8$, in which
$R^7$ or $R^8$ are identical or different and denote hydrogen, straight-chain or branched alkyl having up to 8 carbon atoms or phenyl, or denote straight-chain or branched alkoxy or alkyl in each case having up to 8 carbon atoms, where the latter can be substituted by hydroxyl or halogen or by straight-chain or branched alkoxy having up to 6 carbon atoms,
$R^2$ represents hydrogen, or represents a carboxyl protective group customary in β-lactam chemistry or represents an ester radical which can be cleaved in vivo and their pharmaceutically tolerable salts.

Owing to the presence of the double bonds (=Y), the compounds of the general formula (I) according to the invention can occur as pure syn- or anti-isomers or as mixtures of isomers. The syn-isomers of the compounds of the general formula (I) according to the invention are preferred.

Both the isomer mixtures and the syn- and anti-form of the compounds according to the invention can be employed for the treatment of infectious bacterial diseases.

The compounds of the general formula (I) can be present as free acids, esters, as internal salts or as non-toxic pharmaceutically tolerable salts of the acidic carboxyl groups, such as sodium, potassium, magnesium, calcium, aluminium or ammonium salts, with amines such as di- or tri-lower alkylamines, procaine, dibenzylamine, N,N'-dibenzylethylenediamine, N-benzyl-β-phenyl-ethylamine, N-methyl- and N-ethylmorpholine, 1-ephenamine, dihydroabietylamine, N,N'-bis-dehydroabietylethylenediamine, N-lower alkylpiperidine and other amines which can be used for the formation of salts of penicillins and cephalosporins.

Examples of non-toxic, pharmaceutically tolerable salts of the basic amino groups with inorganic or organic acid radicals which may preferably be mentioned are chloride, bromide, iodide, sulphate, hydrogensulphate, phosphate, carbonate, hydrogencarbonate, or sulphonates such as methylsulphonate, ethanesulphonate, toluenesulphonate, benzenesulphonate, naphthalenedisulphonate, or carboxylates such as acetate, formate, oxalate, tartrate, citrate, maleate, fumarate, benzoate, succinate or lactate.

Amino or oxime protective group in the context of the abovementioned definition in general represents a protective group customary in β-lactam chemistry and from the series comprising: tert-butoxycarbonyl, benzyloxycarbonyl, 2-nitrobenzyloxycarbonyl, 4-nitrobenzyloxycarbonyl, phenylacetyl, allyloxycarbonyl, 2,4-dimethoxybenzyloxycarbonyl, allyloxymethyl,bis-(4-methoxyphenyl)methyl,2-(methylthiomethoxy)-ethoxycarbonyl,trimethyl-, triethyl- or triphenylsilyl, trityl, tert-butyl-dimethylsilyl, tert-butyldiphenylsilyl, [2-(trimethylsilyl)ethoxy]methyl, 1-methyl-2-benzoyl-vinyl, 1-methyl-2-methoxy-vinyl, 1-methyl-2-acetyl-vinyl, 1-methyl-2-(methoxybenzoyl)-vinyl, 1-methyl-2-(2,6-dimethoxybenzoyl)vinyl and 1-methyl-2-ethoxycarbonyl-vinyl.

Carboxyl protective group in the context of the above-mentioned definition represents the carboxyl protective groups customary in β-lactam chemistry. Groups which can be eliminated easily may preferably be mentioned, such as, for example: tert-butyl, 2,2,2-trichloroethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilylethyl, trimethylsilyl, tert-butyl-dimethylsilyl, acetonyl, 1-phenoxyethyl or 2-methyl-2-propenyl.

If $R^2$ represents an ester radical which can be eliminated easily in vivo, pharmaceutically tolerable ester radicals which can be hydrolysed easily in vivo to the free carboxyl groups ($R^2$=H) are meant.

Such ester radicals are well known from the β-lactam field. In most cases, they improve the absorption properties of the β-lactam compounds. Moreover, the radical $R^2$ should be of such a type that it imparts pharmaceutically acceptable properties to a compound of the formula (I) and on cleavage in vivo releases pharmaceutically acceptable fragments.

Examples of such groups are found in German Offenlegungsschrift 2,517,316. Preferred ester groups which can be eliminated in vivo are those of the following formulae:

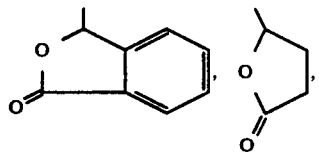, 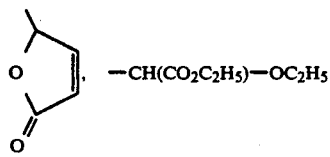

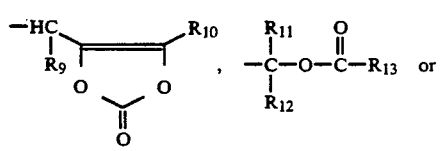

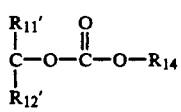

in which

R$^9$ and R$^{10}$ are identical or different and denote hydrogen, phenyl or straight-chain or branched alkyl having up to 4 carbon atoms, R$^{11}$, R$^{11'}$, R$^{12}$ and R$^{12'}$ are identical or different and denote hydrogen or straight-chain or branched alkyl having up to 4 carbon atoms, R$^{13}$ denotes straight-chain or branched alkyl having up to 6 carbon atoms, R$^{14}$ denotes straight-chain or branched alkyl having up to 6 carbon atoms or cyclohexyl.

Preferred compounds of the general formula (I) are those in which

X represents a nitrogen atom or the —CH group, Y represents a group of the formula N—OR$^3$ or CH—R$^4$, in which R$^3$ denotes hydrogen or straight-chain or branched alkyl having up to 6 carbon atoms, which is optionally substituted by fluorine, chlorine, bromine or protected or unprotected carboxyl or amino, R$^4$ denotes hydrogen, phenyl, carboxyl, fluorine, chlorine, bromine or straight-chain or branched alkoxy, alkoxycarbonyl or alkyl in each case having up to 6 carbon atoms, where the latter can be substituted by fluorine, chlorine, bromine, hydroxyl, carboxyl or by straight-chain or branched alkoxy or alkoxycarbonyl in each case having up to 4 carbon atoms, R$^1$ represents a radical of the formula

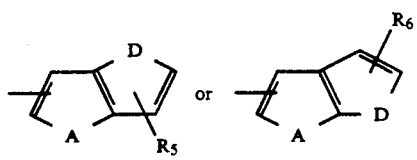

in which

A denotes a sulphur atom and

D denotes the —CH═CH group or a sulphur atom,

R$^5$ and R$^6$ are identical or different and denote fluorine, chlorine, bromine, amino or straight-chain or branched alkoxy or alkyl in each case having up to 4 carbon atoms, where the latter can be substituted by hydroxyl, fluorine, chlorine, methoxy or ethoxy, R$^2$ represents hydrogen, or represents a radical of the formula

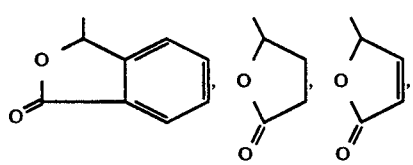

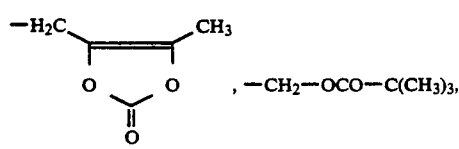

—CH(CH$_3$)—OCOOC$_2$H$_5$, —CH$_2$—OCOCH$_3$,

—CH—(CH$_3$)—O—CO—CH$_3$,

—CH(CH$_3$)—O—COO—CH$_3$,

—CH(CH$_3$)—O—COO—CH(CH$_3$)$_2$,

—CH(CH$_3$)—O—COO—C$_6$H$_{11}$ or

—CH(CO$_2$C$_2$H$_5$)—OC$_2$H$_5$ and their pharmaceutically tolerable salts.

Particularly preferred compounds of the general formula (I) are those in which

X represents a nitrogen atom or the —CH group,

Y represents a group of the formula N—OR$^3$ or —CHR$^4$, in which

R$^3$ denotes hydrogen or straight-chain or branched alkyl having up to 4 carbon atoms, which is optionally substituted by fluorine, chlorine or by protected or unprotected carboxyl or amino, R$^4$ denotes hydrogen or straight-chain or branched alkoxy or alkyl in each case having up to 4 carbon atoms, where the latter can be substituted by hydroxyl, carboxyl, methoxy, ethoxy or propoxy, R$^1$ represents a radical of the formula

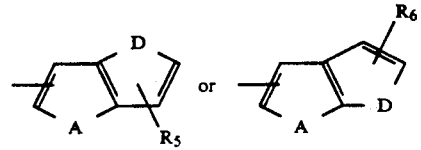

in which

A denotes a sulphur atom and

D denotes the —CH=CH group or a sulphur atom, $R^5$ and $R^6$ are identical or different and denote fluorine, chlorine, bromine, amino or straight-chain or branched alkoxy or alkyl in each case having up to 4 carbon atoms, where the latter can be substituted by hydroxyl, fluorine, chlorine, methoxy or ethoxy, $R^2$ represents hydrogen, or represents a radical of the formula

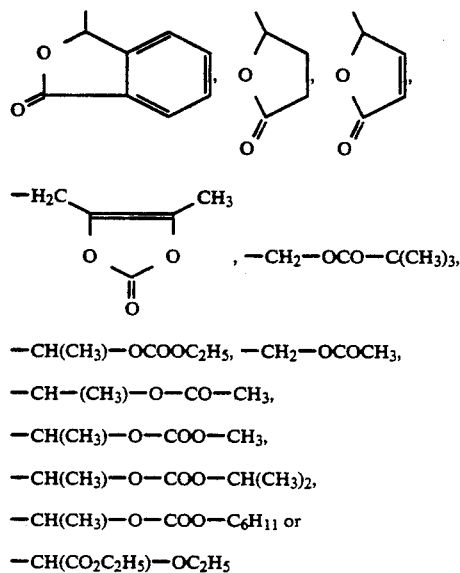

—CH(CH$_3$)—OCOOC$_2$H$_5$,  —CH$_2$—OCOCH$_3$,

—CH—(CH$_3$)—O—CO—CH$_3$,

—CH(CH$_3$)—O—COO—CH$_3$,

—CH(CH$_3$)—O—COO—CH(CH$_3$)$_2$,

—CH(CH$_3$)—O—COO—C$_6$H$_{11}$ or

—CH(CO$_2$C$_2$H$_5$)—OC$_2$H$_5$ and their pharmaceutically tolerable salts.

The sodium salts and the hydrochlorides are very particularly preferred.

A process for the preparation of the compounds of the general formula (I) according to the invention has furthermore been found, characterised in that compounds of the general formula (II)

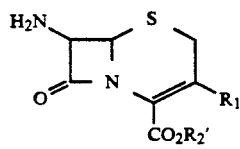
(II)

in which $R^1$ has the abovementioned meaning and $R^{2'}$ represents one of the abovementioned carboxyl protective groups, in particular p-methoxybenzyl, are reacted, if appropriate also with activation of the amine function, with compounds of the general formula (III)

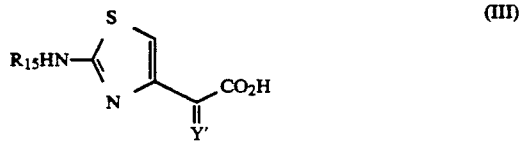
(III)

in which

Y' represents one of the abovementioned groups N—OR' or CHR$^{4'}$, in which $R^{3'}$ has the abovementioned meaning of $R^3$ or represents one of the abovementioned oxime radical, $R^{4'}$ has the abovementioned meaning of $R^4$ or represents protected carboxyl and $R^{15}$ also represents one of the abovementioned amino protective groups, preferably Boc or the trityl radical, in inert solvents, if appropriate with activation of the carboxyl group in the presence of an auxiliary, first to give the compounds of the general formula (IV)

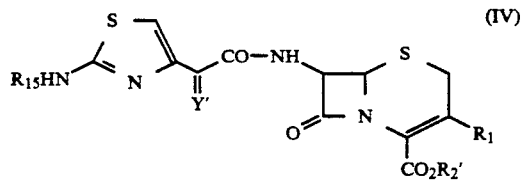
(IV)

in which $R^1$, $R^{2'}$, $R^{15}$ and Y' have the abovementioned meaning, and then the protective group $R^{2'}$, $R^{3'}$, $R^{4'}$ (Y') and $R^{15}$ is eliminated by a customary method, if appropriate in 2 steps, and the desired salts or, from the salts, the free acids, are prepared.

The process according to the invention can be illustrated by way of example by the following equation:

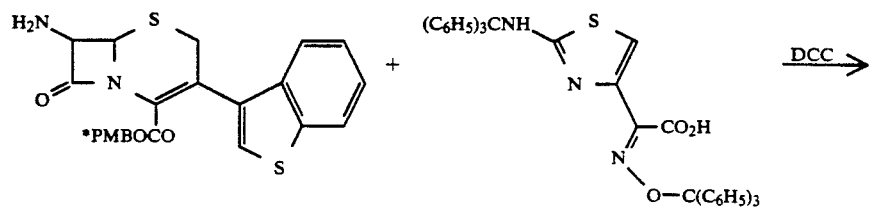

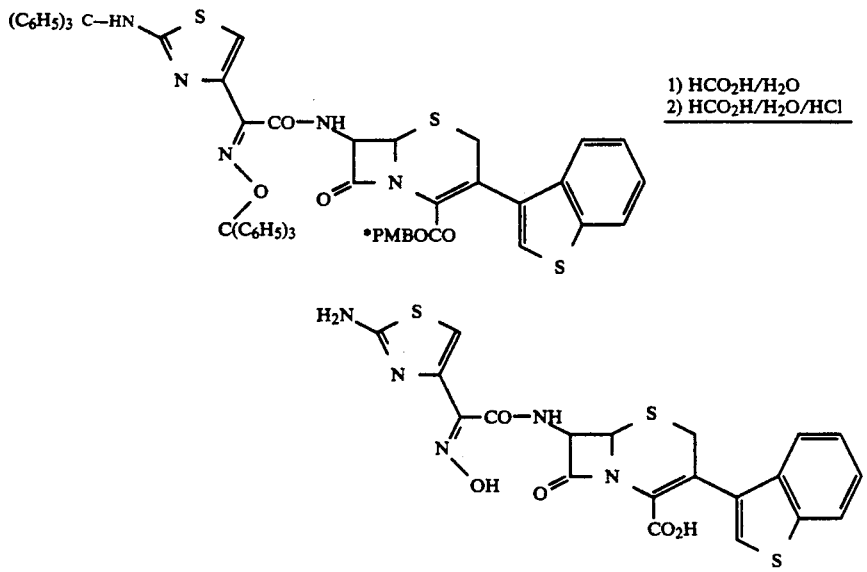

*PMB = p-methoxybenzyl

Suitable solvents are all solvents which do not change under the reaction conditions. These preferably include ethers such as, for example, diethyl ether, dioxane or tetrahydrofuran, or chlorohydrocarbons such as methylene chloride, chloroform or tetrachloromethane, or amides such as dimethylformamide or hexamethylphosphoric triamide, or acetonitrile or acetone. It is also possible to employ mixtures of the solvents mentioned. Methylene chloride is preferred.

The condensation is in general carried out in a temperature range from 0° C. to +60° C., preferably at room temperature and at normal pressure.

The carboxyl group in the compounds of the general formula (III) is in general activated by conversion into a mixed anhydride using chloroformic acid esters or sulphonic acid derivatives, such as, for example, ethyl chloroformate, isobutyl chloroformate or methanesulphonyl chloride, by conversion into the corresponding acid halide, or by conversion into an activated ester, for example using N-hydroxybenzotriazole or dicyclohexylcarbodiimide. Reaction with ethyl chloroformate and methanesulphonyl chloride is preferred.

The amine function of the compounds of the general formula (II) is activated by a customary method, for example by conversion into the corresponding silyl derivatives by reaction with bis(trimethylsilyl)acetamide, N-trimethylsilylacetamide or bis(trimethylsilyl)urea.

Auxiliaries employed are preferably condensing agents which can also be bases, in particular if, for example, the carboxyl group is present activated as the anhydride. The customary condensing agents such as carbodiimides, for example N,N'-diethyl-, N,N'-dipropyl-, N,N'-diisopropyl- or N,N'-dicyclohexylcarbodiimide, N-(3-dimethylaminoisopropyl)-N'-ethylcarbodiimide hydrochloride, or carbonyl compounds such as carbonyldiimidazole, or 1,2-oxazolium compounds such as 2-ethyl-5-phenyl-1,2-oxazolium-3-sulphonate or 2-tert-butyl-5-methyl-isooxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxytris(dimethylamino)phosphonium hexafluorophosphate or, as bases, alkali metal carbonates, for example sodium or potassium carbonate or hydrogencarbonate, or organic bases such as trialkylamines, for example triethylamine, N-ethylmorpholine or N-methylpiperidine are preferred here.

The protective groups are eliminated by a customary method, in the case of the oximes optionally successively, either with organic acids, such as, for example, formic acid, if appropriate in the presence of water or in the presence of water and a protonic acid, such as, for example, hydrochloric acid, preferably with formic acid and water or formic acid, water and hydrochloric acid.

In the case in which $R^3 \neq H$, it is moreover possible to eliminate the amine protective group ($R^{13}$), the carboxyl protective groups ($R^{2'}$) and the protective groups $R^{3'}$ and $R^{4'}$, if appropriate in one step, using trifluoroacetic acid.

The elimination of the protective groups is in general carried out in a temperature range from 0° C. to +80° C., preferably at room temperature.

The eliminations can be carried out both at normal pressure, and at elevated or reduced pressure (for example 0.5 to 5 bar), preferably at normal pressure.

The compounds of the general formula (II) are new, but can be prepared in analogy to processes known from the literature [cf. U.S. Pat. No. 4,855,418; Tetrahedron Lett., Vol. 29, No. 47, 6043–6046, 1988], by reacting, for example, p-methoxybenzyl 7-phenacetylamino-3-trifluoromethanesulphonyl-3-cephem-4-carboxylate of the formula (V)

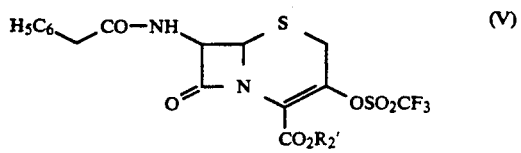

in which $R^{2'}$ has the abovementioned meaning, with compounds of the general formula (VI)

$R^1 - Z$ (VI)

in which

R[1] has the abovementioned meaning and

Z represents an organotin radical defined in the following, in aprotic polar solvents, in the presence of metal halides, phosphines and a catalyst to give compounds of the general formula (VII)

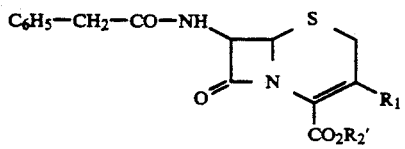

(VII)

in which

R[1] and R[2'] have the abovementioned meaning, and in a last step deblocking the amine function by a customary method, for example by the action of the system 1.} PCl$_5$/pyridine/methylene chloride and 2.) HN(C$_2$H$_5$)$_2$/methanol.

Examples of suitable organotin radicals (Z) are trimethylstannyl, triethylstannyl or tributylstannyl. Tri-n-butylstannyl is preferred.

Suitable metal halides are zinc, lithium and magnesium halides, such as, for example, ZnCl$_2$, ZnBr$_2$, LiCl, LiBr, MgCl$_2$ or MgBr$_2$. ZnCl$_2$ is preferred.

Suitable catalysts are Pd(0) and (II) complexes, such as, for example, bis(dibenzylidene-acetonyl)palladium [(Pd/dba)$_2$], Pd$_2$dba$_3$ x CHCl$_3$ or Pd(OAc)$_2$. Pd$_2$dba$_3$ x CHCl$_3$ is preferred.

Examples of suitable aprotic polar solvents are acetonitrile, dimethyl sulphoxide (DMSO), dimethylformamide (DMF), or ethers such as glyme, dioxane or THF, or acetone, hexamethylphosphoramide, or N-methylpyrrolidone or 1-methyl-2-pyrrolidone. N-Methylpyrrolidone is preferred.

Examples of phosphines which can be employed are triphenylphosphine,tri-(3-fluorophenyl)phosphine,diphenylmethylphosphine, tributylphosphine, tri-(2-thienyl)phosphine or tri-(2-furyl)phosphine. Tri-(2-furyl)phosphine is preferred.

The reaction is carried out in a temperature range from $-30°$ C. to $+90°$ C., preferably at room temperature and at normal pressure.

The compound of the general formula (V) is known per se [J. Org. Chem. 1989, 54, 4962–4966].

The compounds of the general formula (VI) are known in some cases, but can be prepared and employed by processes known from the literature [cf. EP 343,277 A1].

Taking into account the abovementioned definition of R[1], the compounds of the general formula (VII) are new, but can be prepared in analogy to known processes [cf. J. Org. Chem., Vol. 54, No. 20, 1989].

The compounds of the general formula (III) are known per se or can be prepared by a customary method [cf. Tetrahedron, Vol. 34, 2233–2243].

The compounds of the general formula (IV) are new and can be prepared by the abovementioned process.

The compounds of the general formula (I) according to the invention have a broad antibacterial spectrum against Gram-positive and Gram-negative microorganisms coupled with low toxicity. These properties make possible their use as chemotherapeutic active compounds in human and veterinary medicine.

The compounds according to the invention are active against a very broad spectrum of microorganisms. With their aid, Gram-negative and Gram-positive bacteria and bacteria-like microorganisms can be controlled and the diseases produced by these pathogens can be prevented, ameliorated and/or cured.

The compounds according to the invention are particularly active against bacteria and bacteria-like microorganisms. They are therefore particularly highly suitable in human and veterinary medicine for the prophylaxis and chemotherapy of local and systemic infections which are produced by such pathogens.

The present invention includes pharmaceutical preparations which, in addition to non-toxic, inert, pharmaceutically suitable excipients, contain one or more compounds according to the invention or which consist of one or more active compounds according to the invention, and processes for the production of these preparations.

The active compound or compounds may optionally also be present in one or more of the abovementioned excipients in microencapsulated form.

The therapeutically active compounds should preferably be present in the abovementioned pharmaceutical preparations in a concentration of about 0.1 to 99.5 % by weight, preferably of about 0.5 to 95 % by weight, of the total mixture.

Apart from the compounds according to the invention, the abovementioned pharmaceutical preparations may also contain other pharmaceutical active compounds.

In general it has proved advantageous both in human and in veterinary medicine to administer the active compound or compounds according to the invention in total amounts of about 0.5 to about 500 mg/kg, preferably 5 to 100 mg/kg of body weight every 24 hours, if appropriate in the form of several individual doses, to achieve the desired results. A single dose preferably contains the active compound or compounds according to the invention in amounts of about 1 to about 80 mg/kg, in particular 3 to 30 mg/kg, of body weight.

The new compounds can be combined in the customary concentrations and preparations together with the feed or lactamase inhibitors, for example with penicillins which are particularly resistant to penicillinase and clavulanic acid. Such a combination would be, for example, that with oxacillin or dicloxacillin.

The compounds according to the invention can be combined, for the purpose of increasing the spectrum of action and also to achieve an increase in action, with aminoglycoside antibiotics, such as, for example, gentamicin, sisomicin, kanamycin, amikacin or tobramycin.

$^1$H-NMR data are available for all compounds.

Starting Compounds

EXAMPLE 1

3-Benzo[b]thienyl-tri-n-butyl-stannane

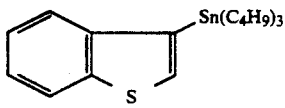

32.0 9 (150 mmol) of 3-bromo-benzo[b]thiophene are added dropwise at $-78°$ C. to a solution of 150 mmol of n-butyllithium in 500 ml of anhydrous THF. The mixture is stirred at $-78°$ C. for 1 h, 52.1 g (160 mmol) of tri-n-butyl-tin chloride are added and the mixture is allowed to warm to room temperature. For working-up, saturated ammonium chloride solution is added and the mixture is extracted with ether. After chromatography on silica gel using petroleum ether, 14.8 g (23 % of theory) of the title compound are obtained.

EXAMPLE II p-Methoxybenzyl 3-(3-benzo[b]thienyl)-7β-phenacetylamino-3-cephem-4-carboxylate

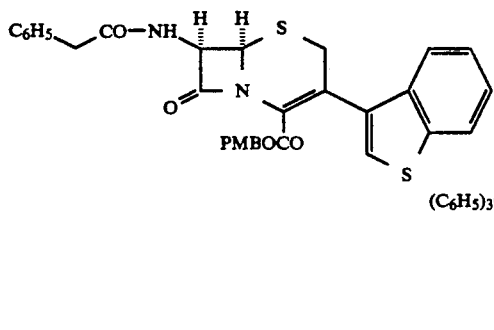

4.7 g (8.0 mmol) of p-methoxybenzyl 7β-phenacetylamino-3-trifluoromethane-sulphonyloxy-3-cephem-4-carboxylate are allowed to react overnight at 50° C. with 3.4 g (8.0 mmol) of the compound from Example I, 1.9 g (13.9 mmol) of anhydrous zinc chloride, 0.34 g of tri-2-furylphosphine and 0.35 g (0.34 mmol) of tris-(dibenzylideneacetone)-dipalladium-chloroform in 130 ml of anhydrous N-methylpyrrolidone under argon. The mixture is then poured into 400 ml of water and the precipitate which deposits is filtered off with suction. The residue, dissolved in 400 ml of methylene chloride, is dried using sodium sulphate and, after removing the solvent, chromatographed on silica gel using toluene/ethyl acetate (9:1).

Yield: 3.2 g (70 % of theory).

EXAMPLE III p-Methoxybenzyl 7β-amino-3-(3-benzo[b]thienyl)-3-cephem-4-carboxylate

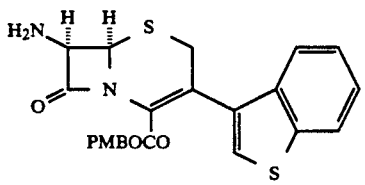

3.3 g (15.8 mmol) of phosphorus pentachloride are added at −20° C. to a solution of 4.4 g (7.7 mmol) of the compound from Example II and 1.6 ml (19.8 mmol) of pyridine in 80 ml of anhydrous methylene chloride. The mixture is stirred at −20° C. for 5 min, at 0° C. for 10 min, at 15° C. for 1 h and then cooled to −78° C. 80 ml of methanol cooled to −78° C. are rapidly added. The solution is stirred at −78° C. for 5 min, at 0° C. for 10 min and at 15° C. for 25 min. After cooling to −15° C., 0.95 ml (9.2 mmol) of diethylamine is added and the mixture is kept at this temperature for 10 min. For working-up, it is poured into 150 ml of saturated sodium hydrogencarbonate solution and extracted with methylene chloride. The combined organic phases are washed with sodium hydrogencarbonate solution and water, dried using sodium sulphate and concentrated. The residue is chromatographed on silica gel using toluene/ethyl acetate (3:1).

Yield: 2.9 g (83 % of theory)

EXAMPLE IV p-Methoxybenzyl 3-(3-benzo[b]thienyl)-7β-[2-(2-tritylamino-4-thiazolyl)-2-syn-trityloxyimino-acetylamino]-3-cephem-4-carboxylate

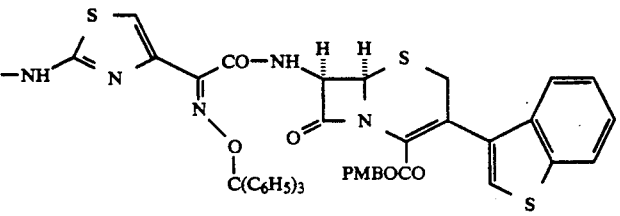

A solution of 6.9 g (10 mmol) of 2-(2-tritylamino-4-thiazolyl)-2-syn-trityloxyimino-acetic acid in 100 ml of methylene chloride is stirred with 1.4 g (7 mmol) of dicyclohexylcarbodiimide at room temperature for 2 h. 1.7 g (4 mmol) of the compound from Example III are added and the mixture is stirred at room temperature overnight. After removing the solvent by distillation, the residue is chromatographed on silica gel using toluene.

Yield: 2.8 g (64 % of theory)

EXAMPLE V p-Methoxybenzyl 3-(3-benzo[b]thienyl)-7β-[2-(2-t-butyloxycarbonylamino-4-thiazolyl)-2-syn-methoxyimino-acetylamino]-3-cephem-4-carboxylate

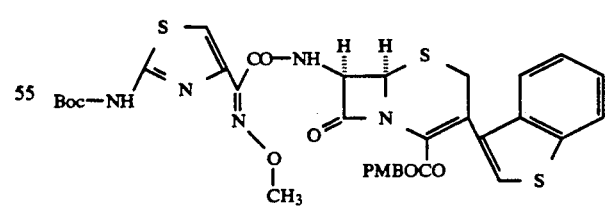

A solution of 0.6 g (1.3 mmol) of the compound from Example III, 1.2 g (4 mmol) of 2-(2-t-butyloxycarbonylamino-4-thiazolyl)-2-syn-methoxyiminoacetic acid and 0.85 g (4 mmol) of dicyclohexylcarbodiimide in 40 ml of acetonitrile is stirred overnight. It is concentrated and chromatographed on silica gel using toluene/ethyl acetate (5:1).

Yield: 0.8 g (85 % of theory)

PREPARATION EXAMPLES

Example 1 p-Methoxybenzyl 7β-[2-(2-amino-4-thiazolyl)-2-synhydroxyimino-acetylamino]-3-(3-benzo[b]thienyl)-3-cephem-4-carboxylate

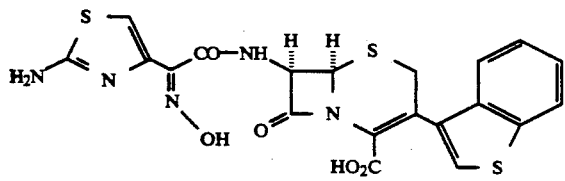

2.8 g (2.5 mmol) of the compound from Example IV are stirred with 20 ml of 90% strength formic acid at room temperature for 1 h. 1 ml of conc. hydrochloric acid is then added and the mixture is stirred at room temperature for a further 2 h. It is concentrated to dryness in vacuo and chromatographed on HP-20 using water/acetonitrile.

Yield: 1.0 g (80% of theory)

$^1$H-NMR (DCOOD): 3.98 (s, 2H, 2-H); 5.46 (d, J =5 Hz, 1H, 6-H); 6.13 (d, J=5 Hz, 1H, 7-H); 7.42 (s, 1H, 7'-Ar-H); 7.35–7.45 (m, 3H, 3'-Ar-H), 7.78–7.89 (m, 2H, 3'-Ar-H).

Example 2 p-Methoxybenzyl 7β-[2-(2-amino-4-thiazolyl)-2-syn-methoxyimino-acetylamino]-3-(3-benzo[b]thienyl-3-cephem-4carboxylate (trifluoroacetate)

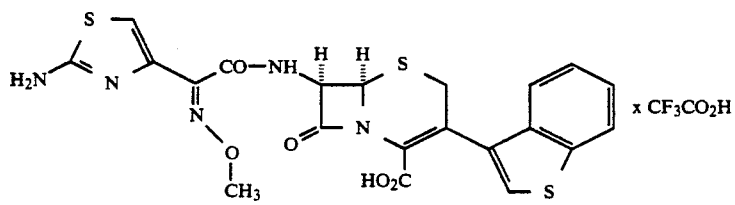

0.8 g (1.1 mmol) of the compound from Example V is treated with a mixture of 1 ml of anisole and 50 ml of trifluoroacetic acid at room temperature for 1 h. The trifluoroacetic acid is then stripped off in vacuo and the residue is stirred with diisopropyl ether.

Yield: 0.6 g (87 % of theory)

$^1$H-NMR (DCOOD): 4.00 (s, 2H, 2-H); 4.17 (s, 3H, OCH$_3$); 5.44 (d, J=5 Hz, 1H, 6-H), 6.12 (d, J=5 Hz, 1H, 7-H); 7.37 (s, 1H; 7'-Ar-H); 7.40–7.45 (m, 3H, 3'-Ar-H); 7.80–7.90 (m, 2H, 3'-Ar-H).

We claim:

1. Compounds of the formula

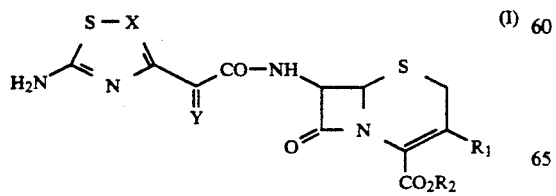

in which

X represents a nitrogen atom of the —CH group,

Y represents a group of the formula N—OR$^3$ or CHR$^4$, in which

R$^3$ denotes hydrogen, straight-chain or branched alkenyl, alkinyl or alkyl in each case having up to 8 carbon atoms, where the latter can optionally be substituted by halogen or by protected or unprotected carboxyl or amino, the carboxyl being protected by a protecting group selected from the group consisting of tert-butyl, 2,2,2-trichloroethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilylethyl, trimethylsilyl, tert-butyldimethylsilyl, acetonyl, 1-phenoxyethyl and 2-methyl-2-propenyl, and the amino being protected by a protecting group selected from the group consisting of tertbutoxycarbonyl, benzyloxycarbonyl, 2-nitrobenzyloxycarbonyl, 4-nitrobenzyloxycarbonyl, phenylacetyl, allyloxycarbonyl, 2,4-dimethoxybenzyloxycarbonyl, allyloxymethyl, bis-(4-methoxyphenyl)methyl, 2-(methylthiomethoxy)ethoxycarbonyl, trimethylsilyl, triethylsilyl, triphenylsilyl, trityl, tert-butyl-dimethylsilyl, tert-butyldiphenylsilyl, (2-(trimethylsilyl)ethoxy)-methyl, 1-methyl-2-benzoylvinyl, 1-methyl-2-methoxy-vinyl, 1-methyl-2-acetylvinyl, 1-methyl-2-(methoxybenzoyl)-vinyl, 1-methyl-2-(2,6-dimethoxybenzoyl)vinyl and 1-methyl-2-ethoxycarbonyl-vinyl, R$^4$ denotes hydrogen, phenyl, naphthyl, protected or unprotected carboxyl, the carboxyl being protected by a protecting group selected from the group consisting of tert-butyl, 2,2,2-trichloroethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilylethyl, trimethylsilyl, tert-butyldimethylsilyl, acetonyl, 1-phenoxyethyl and 2-methyl-2-propenyl, halogen or straight-chain or branched alkoxycarbonyl, alkoxy, alkenyl or alkyl in each case having up to 8 carbon atoms, where the latter can optionally be substituted by halogen, hydroxyl, nitro, cyano or carboxyl or by straight-chain or branched alkoxy or alkoxycarbonyl in each case having up to 6 carbon atoms, R$^1$ represents a radical of the formula

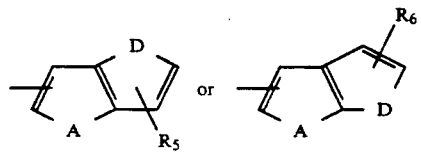

in which

A represents oxygen or sulphur and D represents the group —CH=CH or an oxygen or sulphur atom, and $R^5$ and $R^6$ are identical or different and denote halogen, trifluoromethyl, trifluoromethoxy, hydroxyl or a group of the formula —$NR^7R^8$, in which $R^7$ and $R^8$ are identical or different and denote hydrogen, straight-chain or branched alkyl having up to 8 carbon atoms or phenyl, or denote straight-chain or branched alkoxy or alkyl in each case having up to 8 carbon atoms, where the latter is substituted by hydroxyl or halogen or by straight-chain or branched alkoxy having up to 6 carbon atoms, $R^2$ represents hydrogen or represents a carboxyl protective group selected from the group consisting of tert-butyl, 2,2,2-trichloroethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilylethyl, trimethylsilyl, tert-butyl-dimethylsilyl, acetonyl, 1-phenoxyethyl and 2-methyl-2-propenyl, or represents an ester radical selected from the group consisting of those of the formulae:

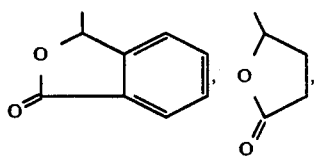

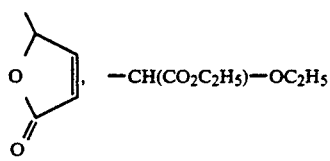

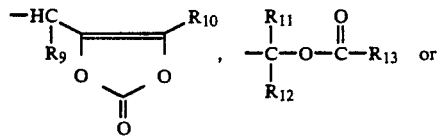

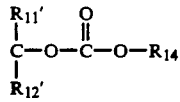

in which $R^9$ and $R^{10}$ are identical or different and denote hydrogen, phenyl or straight-chain or branched alkyl having up to 4 carbon atoms, $R^{11}$, $R^{11'}$, $R^{12'}$ are identical or different and denote hydrogen or straight-chain or branched alkyl having up to 4 carbon atoms, $R^{13}$ denotes straight-chain or branched alkyl having up to 6 carbon atoms, and $R^{14}$ denotes straight-chain or branched alkyl having up to 6 carbon atoms or cyclohexyl, and their pharmaceutically tolerable salts.

2. Compounds according to claim 1, in which $R^2$ represents:
an ester group of the following formulae:

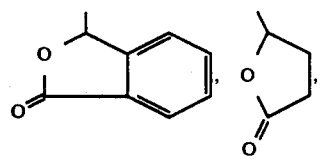

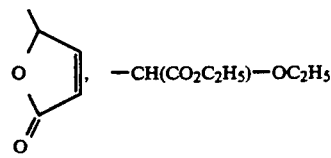

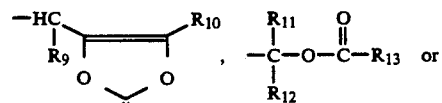

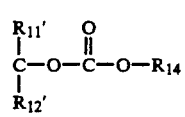

in which $R^9$ and $R^{10}$ are identical or different and denote hydrogen, phenyl or straight-chain or branched alkyl having up to 4 carbon atoms, $R^{11}$, $R^{11'}$, $R^{12}$ and $R^{12'}$ are identical or different and denote hydrogen or straight-chain or branched alkyl having up to 4 carbon atoms, $R^{13}$ denotes straight-chain or branched alkyl having up to 6 carbon atoms, $R^{14}$ denotes straight-chain or branched alkyl having up to 6 carbon atoms or cyclohexyl.

3. Compounds of the formula

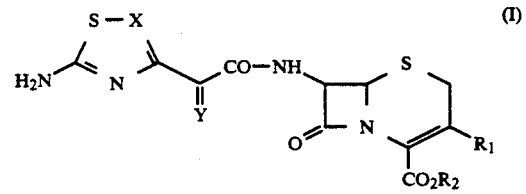

in which

X represents a nitrogen atom or the —CH group,

Y represents a group of the formula N—$OR^3$ or $CHR^4$, in which $R^3$ denotes hydrogen or straight-chain or branched alkyl having up to 6 carbon atoms, which is optionally substituted by fluorine, chlorine, bromine or protected or unprotected carboxyl or amino, the carboxyl being protected by a protecting group selected from the group consisting of tertbutyl, 2,2,2-trichloroethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilylethyl, trimethylsilyl, tert-butyldimethylsilyl, acetonyl, 1-phenoxyethyl and 2-methyl-2-propenyl, and the amino being protected by a protecting group selected from the group consisting of tert-butoxycarbonyl, benzyloxycarbonyl, 2-nitrobenzyloxycarbonyl, 4-nitrobenzyloxycarbonyl, phenylacetyl, allyloxycarbonyl, 2,4-dimethoxybenzyloxycarbonyl, allyloxymethyl, bis-(4-methoxyphenyl)methyl, 2-(methylthiomethoxy)-ethoxycarbonyl, trimethylsilyl, triethylsilyl, triphenylsilyl, trityl, tert-butyldimethylsilyl, tert-butyldiphenylsilyl, (2-(trimethylsilyl)ethoxy)methyl, 1-methyl-2-benzoylvinyl, 1-methyl-2-methoxy-vinyl, 1-methyl-2-acetylvinyl, 1-methyl-2-(methoxybenzoyl)-vinyl, 1-methyl-2-(2,6-dimethoxybenzoyl)vinyl and 1-methyl-2-ethoxycarbonyl-vinyl, $R^4$ denotes hydrogen, phenyl, carboxyl, fluorine chlorine, bromine or straight-chain or branched alkoxy, alkoxycarbonyl or alkyl in each case having up to 6 carbon atoms, where the latter can be substituted by fluorine, chlorine, bromine, hydroxyl, carboxyl or by straight-chain or branched alkoxy or alkoxycarbonyl in each case having up to 4 carbon atoms, $R^1$ represents a radical of the formula

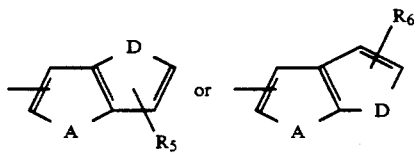

in which

A denotes a sulphur atom an

D denotes the —CH=CH group or a sulphur atom, $R^5$ and $R^6$ are identical or different and denote fluorine, chlorine, bromine, amino or straight-chain or branched alkoxy or alkyl in each case having up to 4 carbon atoms, where the latter can be substituted by hydroxyl, fluorine, chlorine, methoxy or ethoxy, $R^2$ represents hydrogen or represents a radical of the formula

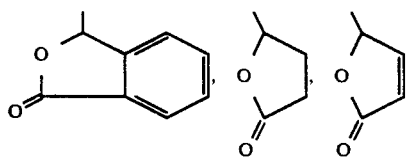

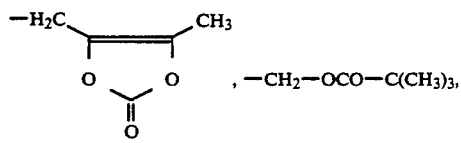

—CH(CH₃)—OCOOC₂H₅, —CH₂—OCOCH₃,

—CH—(CH₃)—O—CO—CH₃,

—CH(CH₃)—O—COO—CH₃,

—CH(CH₃)—O—COO—CH(CH₃)₂,

—CH(CH₃)—O—COO—C₆H₁₁ or

—CH(CO₂C₂H₅)—OC₂H₅ and their pharmaceutically tolerable salts.

4. Compounds of the formula

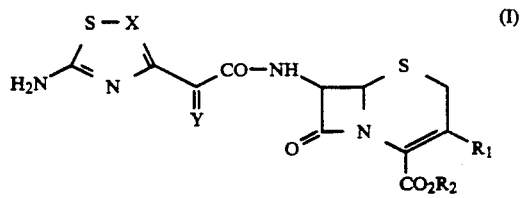

in which

X represents a nitrogen atom or the —CH group,

Y represents a group of the formula N—OR³ or CHR⁴, in which

R³ denotes hydrogen or straight-chain or branched alkyl having up to 4 carbon atoms, which is optionally substituted by fluorine, chlorine, or by protected or unprotected carboxyl or amino, the carboxyl being protected by a protecting group selected from the group consisting of tert-butyl, 2,2,2-trichloroethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilyl, acetonyl, 1-phenoxyethyl and 2-methyl-2-propenyl, and the amino being protected by a protecting group selected from the group consisting of tert-butoxycarbonyl, benzyloxycarbonyl, 2-nitrobenzyloxycarbonyl, 4-nitrobenzyloxycarbonyl, phenylacetyl, allyloxycarbonyl, 2,4-dimethoxybenzyloxycarbonyl, allyloxymethyl, bis-(4-methoxyphenyl)methyl, 2-(methylthiomethoxy)-ethoxycarbonyl, trimethylsilyl, triethylsilyl, triphenylsilyl, trityl, tert-butyldimethylsilyl, tert-butyldiphenylsilyl, (2-(trimethylsilyl)ethoxy)methyl, 1-methyl-2-benzoylvinyl, 1-methyl-2-methoxy-vinyl, 1-methyl-2-acetylvinyl, 1-methyl-2-(methoxybenzoyl)-vinyl, 1-methyl-2-(2,6-dimethoxybenzoyl)vinyl and 1-methyl-2-ethoxycarbonyl-vinyl, $R^4$ denotes hydrogen or straight-chain or branched alkoxy or alkyl in each case having up to 4 carbon atoms, where the latter can be substituted by hydroxyl, carboxyl, methoxy, ethoxy or propoxy, $R^1$ represents a radical of the formula

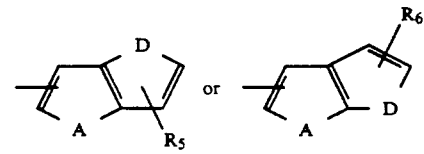

in which

A denotes a sulphur atom and

D denotes the —CH=CH group or a sulphur atom, $R^5$ and $R^6$ are identical or different and denote fluorine, chlorine, bromine, amino or straight-chain or branched alkoxy or alkyl in each case having up to 4 carbon atoms, where the latter can be substituted by hydroxyl, fluorine, chlorine, methoxy or ethoxy, $R^2$ represents hydrogen or represents a radical of the formula

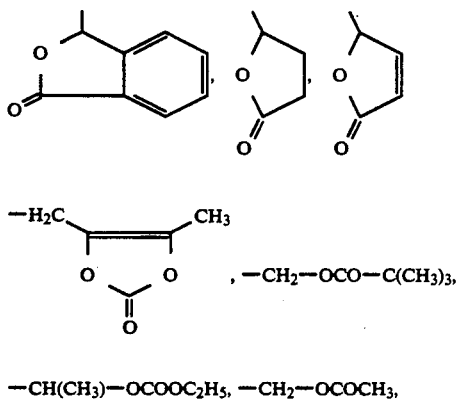

—CH(CH₃)—OCOOC₂H₅, —CH₂—OCOCH₃,

-continued
—CH—(CH₃)—O—CO—CH₃,

—CH(CH₃)—O—COO—CH₃,

—CH(CH₃)—O—COO—CH(CH₃)₂,

—CH(CH₃)—O—COO—C₆H₁₁ or

—CH(CO₂C₂H₅)—OC₂H₅ and their pharmaceutically tolerable salts.

5. An antibacterial composition comprising an antibacterially effective amount of a compound or salt according to claim 1 and a pharmaceutically acceptable excipient.

6. A method of combatting bacteria which comprises applying to such bacteria or to a bacteria habitat an antibacterially effective amount of a compound or salt according to claim 1.

* * * * *

UNITED STATES PATENT AND TRADEMARK OFFICE
CERTIFICATE OF CORRECTION

PATENT NO. : 5,276,024
DATED : January 4, 1994
INVENTOR(S) : Schneider, et al.

It is certified that error appears in the above-indentified patent and that said Letters Patent is hereby corrected as shown below:

Col. 15, line 57  After " $R^{11'}$, " insert -- $R^{12}$, and --

Col. 18, line 25  After " 2,4-dimethoxybenzyl, " delete " trimethylsilyl " and substitute -- trimethylsilylethyl, trimethylsilyl, tert-butyldimethylsilyl, --

Signed and Sealed this

Twenty-fifth Day of March, 1997

Attest:

BRUCE LEHMAN

Attesting Officer

Commissioner of Patents and Trademarks